(12) United States Patent
Auernhammer

(10) Patent No.: US 9,492,648 B2
(45) Date of Patent: Nov. 15, 2016

(54) VALVE ELEMENT

(75) Inventor: Daniel Auernhammer, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 176 days.

(21) Appl. No.: 14/114,765

(22) PCT Filed: May 4, 2012

(86) PCT No.: PCT/EP2012/058264
§ 371 (c)(1),
(2), (4) Date: Oct. 30, 2013

(87) PCT Pub. No.: WO2012/152703
PCT Pub. Date: Nov. 15, 2012

(65) Prior Publication Data
US 2014/0054489 A1  Feb. 27, 2014

(30) Foreign Application Priority Data
May 6, 2011 (EP) .................................. 11165124

(51) Int. Cl.
*A61M 5/20* (2006.01)
*A61M 39/24* (2006.01)
(Continued)

(52) U.S. Cl.
CPC ............... *A61M 39/24* (2013.01); *A61M 5/19* (2013.01); *A61M 5/2066* (2013.01);
(Continued)

(58) Field of Classification Search
CPC ............. Y10T 29/49412; A61M 39/24; A61M 5/2066; A61M 5/2448; A61M 5/19;
(Continued)

(56) References Cited

U.S. PATENT DOCUMENTS 2,675,758 A * 4/1954 Hughes .................. F04B 9/127
100/907
2,781,780 A * 2/1957 Zahradka .............. F15B 13/043
137/881
(Continued)

FOREIGN PATENT DOCUMENTS

DE  WO 2009156103 A1 * 12/2009 ........ B01L 3/502738
EP  0710487  5/1996
(Continued)

OTHER PUBLICATIONS

International Search Report for Int. App. No. PCT/EP2012/058264, completed Aug. 17, 2012.
(Continued)

*Primary Examiner* — Marina Tietjen
(74) *Attorney, Agent, or Firm* — McDonnell Boehnen Hulbert & Berghoff LLP

(57) ABSTRACT

An apparatus is presented comprising a first part comprising a sealing structure, a membrane being attached to said first part and a second part being attached to said membrane, wherein said second part comprises a valve area with a first opening and a second opening, wherein said valve area is located in the area of said sealing structure, wherein said valve area is configured to allow for a fluidic communication between said first opening and said second opening and wherein said sealing structure is configured to allow for an interruption of said fluidic communication between said first opening and said second opening.

10 Claims, 11 Drawing Sheets

(51) Int. Cl.
*F16K 99/00* (2006.01)
*A61M 5/19* (2006.01)
*A61M 5/24* (2006.01)
*A61M 5/34* (2006.01)
*A61M 5/31* (2006.01)

(52) U.S. Cl.
CPC ............ *A61M 5/2448* (2013.01); *A61M 5/345* (2013.01); *A61M 5/347* (2013.01); *A61M 5/348* (2013.01); *A61M 2005/2407* (2013.01); *A61M 2005/2474* (2013.01); *A61M 2005/2496* (2013.01); *A61M 2005/3118* (2013.01); *A61M 2005/3128* (2013.01); *A61M 2039/2433* (2013.01); *A61M 2205/50* (2013.01); *A61M 2205/502* (2013.01); *A61M 2205/52* (2013.01); *Y10T 29/49412* (2015.01)

(58) Field of Classification Search
CPC .................. A61M 5/345; A61M 5/348; A61M 5/347; A61M 2039/2433; A61M 2205/50; A61M 2005/247; A61M 2005/2474; A61M 2005/2496; A61M 2005/2407; A61M 2005/3118; A61M 2005/3128; A61M 2205/502; A61M 2205/52; F16K 99/0005; F16K 99/0015; F16K 99/0086
USPC .................. 251/359, 331, 335.2, 61.1–61.5; 604/506, 131
See application file for complete search history.

(56) References Cited

U.S. PATENT DOCUMENTS

| | | | | |
|---|---|---|---|---|
| 2,803,265 A * | 8/1957 | Coffey | ................. | F04B 53/103 137/516.21 |
| 3,211,416 A * | 10/1965 | Billeter | ................. | B67D 1/1466 137/315.05 |
| 3,310,282 A * | 3/1967 | Boteler | ................. | F16K 7/126 137/637.2 |
| 3,376,887 A * | 4/1968 | Boteler | ................. | F16K 7/126 137/316 |
| 4,221,361 A * | 9/1980 | Weingarten | ................. | F16K 7/12 137/625.4 |
| 4,376,315 A * | 3/1983 | Badger | ................. | B64D 11/02 251/5 |
| 4,721,133 A * | 1/1988 | Sundblom | ................. | F16K 11/022 137/883 |
| 4,930,747 A * | 6/1990 | Nakamura | ................. | F16K 31/0655 251/129.15 |
| 5,065,978 A * | 11/1991 | Albarda | ................. | B41J 2/17596 251/129.17 |
| 5,127,625 A * | 7/1992 | Kleinhappl | ................. | F16K 31/06 251/129.17 |
| 5,245,753 A * | 9/1993 | Akikusa | ................. | F02M 69/54 29/454 |
| 5,265,843 A * | 11/1993 | Kleinhappl | ................. | F16K 31/06 251/129.17 |
| 5,335,696 A * | 8/1994 | McKenzie | ................. | F16K 7/126 137/863 |
| 5,383,646 A | 1/1995 | Weingarten | | |
| 5,431,185 A | 7/1995 | Shannon et al. | | |
| 5,453,097 A | 9/1995 | Paradis | | |
| 5,660,370 A * | 8/1997 | Webster | ................. | F16K 7/17 137/884 |
| 5,695,120 A * | 12/1997 | Kingsford | ................. | B05B 9/03 137/625.26 |
| 5,769,387 A * | 6/1998 | Perez C. | ................. | F16K 7/17 251/61.1 |
| 5,791,631 A * | 8/1998 | Martin | ................. | F23N 1/007 251/210 |
| 5,839,467 A * | 11/1998 | Saaski | ................. | B01D 61/18 137/501 |
| 5,964,446 A * | 10/1999 | Walton | ................. | G05D 16/0633 137/556 |
| 5,967,173 A * | 10/1999 | Kingsford | ................. | F16K 11/048 137/312 |
| 6,000,416 A * | 12/1999 | Kingsford | ................. | F16K 41/103 137/1 |
| 6,079,692 A * | 6/2000 | Powell | ................. | F16K 7/16 251/331 |
| 6,086,039 A * | 7/2000 | Sievers | ................. | F16K 31/1221 251/333 |
| 6,258,062 B1 * | 7/2001 | Thielen | ................. | A61M 5/30 604/141 |
| 6,749,136 B1 * | 6/2004 | Wilson | ................. | B05B 12/04 239/569 |
| 6,837,484 B2 * | 1/2005 | Kingsford | ................. | F16K 41/103 251/324 |
| 6,994,319 B2 * | 2/2006 | Yudovsky | ................. | C23C 16/45544 251/263 |
| 7,007,916 B2 * | 3/2006 | Lee | ................. | F16K 31/402 251/30.02 |
| 7,168,675 B2 * | 1/2007 | Cabuz | ................. | F16K 31/02 251/129.01 |
| 7,267,669 B2 * | 9/2007 | Staunton | ................. | A61M 5/14228 137/512.4 |
| 7,296,780 B1 * | 11/2007 | Hung | ................. | B05B 1/3026 239/526 |
| 8,235,352 B2 * | 8/2012 | Irwin | ................. | F16K 31/402 251/14 |
| 8,973,891 B2 * | 3/2015 | Maeda | ................. | F02B 37/16 137/907 |
| 2005/0238506 A1 * | 10/2005 | Mescher | ................. | A61M 5/14276 417/413.1 |
| 2007/0219480 A1 * | 9/2007 | Kamen | ................. | G05D 7/0647 604/20 |
| 2010/0185142 A1 * | 7/2010 | Kamen | ................. | A61M 5/14224 604/66 |
| 2011/0114869 A1 * | 5/2011 | Schaeffer | ................. | B01L 3/502738 251/366 |
| 2013/0277591 A1 * | 10/2013 | Scheibe | ................. | F16K 31/52 251/279 |

FOREIGN PATENT DOCUMENTS

| | | |
|---|---|---|
| EP | 1897585 | 3/2008 |
| EP | 1993634 B1 | 4/2011 |
| JP | 2009-525825 A | 7/2009 |

OTHER PUBLICATIONS

Chinese Office Action for CN App. No. 201280031545.8, issued Feb. 1, 2016.
Chinese Search Report for CN App. No. 201280031545.8, dated Jan. 25, 2016.
Japanese Office Action for JP App. No. 2014-508827, mailed Feb. 9, 2016.

* cited by examiner

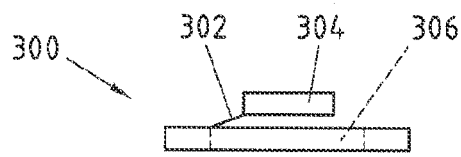
Fig.12c
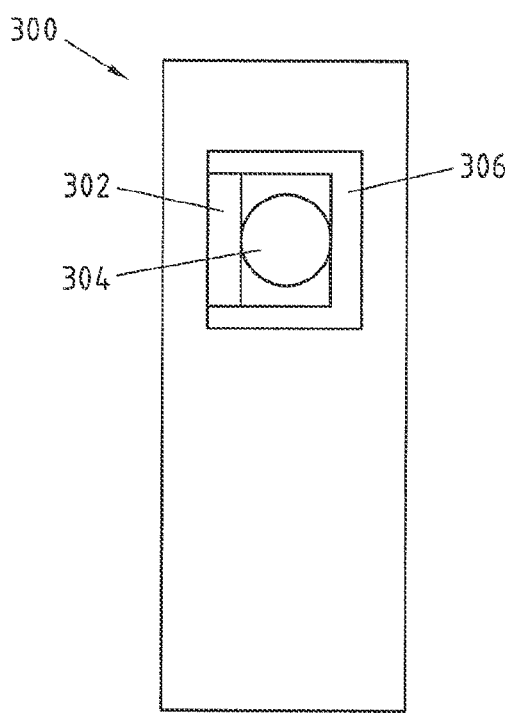 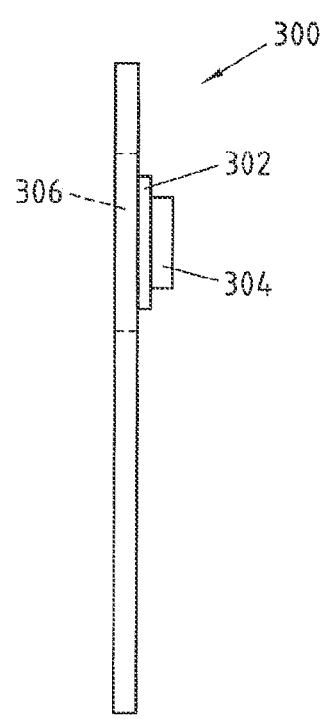
Fig.12a            Fig.12b

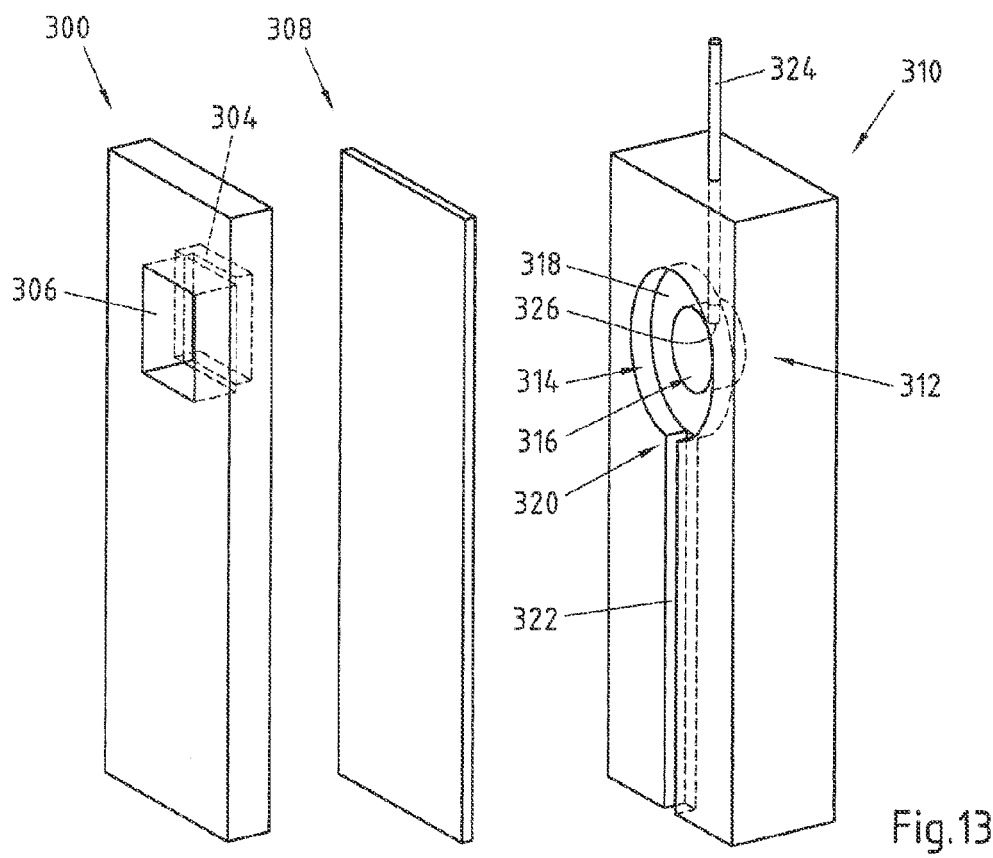
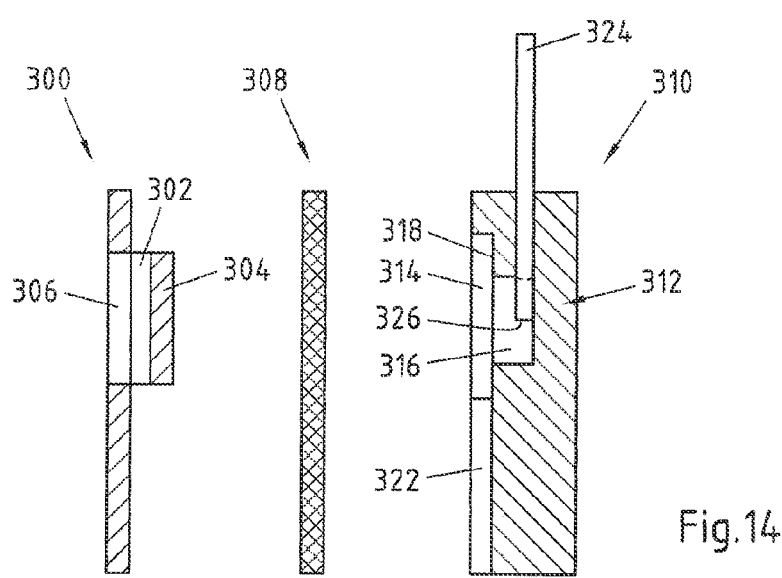

VALVE ELEMENT

CROSS REFERENCE TO RELATED APPLICATIONS

The present application is a U.S. National Phase Application pursuant to 35 U.S.C. §371 of International Application No. PCT/EP2012/058264 filed May 4, 2012, which claims priority to European Patent Application No. 11165124.6 filed May 6, 2011. The entire disclosure contents of these applications are herewith incorporated by reference into the present application.

FIELD OF INVENTION

The present patent application relates to medical devices of delivering at least two drug agents from separate reservoirs. Such drug agents may comprise a first and a second medicament. The medical device includes a dose setting mechanism for delivering the drug automatically or manually by the user.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

For the implementation of the fluidic structures to guide the liquids within medical devices, for example to guide a medicament from its reservoir to the dose dispenser, certain control elements are needed. Those control elements allow for precisely controlling the amount of liquid ejected or for stopping the liquid from escaping the reservoir when the device is not in use. Those tasks are generally solved with valves.

In the state of the art umbrella valves are known, for example. They are being used avoid an uncontrolled outflow of the liquids through the fluidic structures.

The umbrella valves, of course, have to be placed within the actual pathway of a fluidic structure in order to be able to retain the liquid in the reservoirs for example. Umbrella valves have to be made from an elastic material, elastomere, for example. In order to control the behaviour of the umbrella valves, softening agents are often added. This way the material properties of the umbrella valves can be adjusted. Due to the direct contact of the valves with the liquids an accumulation of these agents within the liquid cannot be precluded. In case of medical devices, this can trigger side effects if those agents are injected with the actual medicament.

In order to assemble devices comprising such valves, glues might be used to attach small parts like the valve to the device. This leads to a further risk of a contamination of the guided liquids with unwanted chemicals.

More over the use of such valve elements complicates the production of devices comprising such valves. Since the dimensions of the valves are dictated by the dimensions of the fluidic structures, into which the valves are inserted, time and cost consuming pick-and-place operations of small parts, like said valves, are necessary during the assembly.

The invention faces the technical problem of avoiding the contamination of liquids by valve elements, in particular the contamination of medicaments within medical devices, and facilitating the production of devices comprising valve elements.

The technical problem is solved by an apparatus comprising a first part comprising a sealing structure, a membrane being held against said first part and a second part being held against said membrane, wherein said second part comprises a valve area with a first opening and a second opening, wherein said valve area is located in the area of said sealing structure, wherein said valve area is configured to allow for a fluidic communication between said first opening and said second opening and wherein said sealing structure is configured to allow for an interruption of said fluidic communication between said first opening and said second opening.

The first part comprises the sealing structure, which can in particular be a spring and a retaining element, while this first part is separated from the second part by the membrane. This way the material properties of the sealing structure can be nearly arbitrarily adjusted without affecting the fluid, passing the valve area through the second part.

Thus the sealing structure can for example comprise softening agents without negatively affecting the liquid, because the softening agent is not in direct contact with the second part and thus with the liquid.

The liquid preferably enters the second part through the first opening and this way enters the valve area. Here the liquid can be retained from further flowing into the second opening by the sealing structure of the first part via the membrane in between the first part and the second part. The sealing structure also allows for the liquid to outflow from the valve area via the second opening. The sealing structure preferably exerts a pressure on the membrane, which first interrupts the fluidic communication between the first and the second opening. The sealing structure can be pulled or pushed away from the membrane, for example by external forces or by the pressure of the liquid itself. This way the sealing structure and the membrane are not interrupting the fluidic communication between the first and the second opening. Since the sealing structure is located in the area of the valve area, the sealing structure can easily effect the position of the membrane in said area relatively to the valve area.

Preferably the membrane is an impermeable barrier. This way it can be easily guaranteed that the liquid remains in the second part and that no contaminations from the side of the first part can enter the liquid. The permeability of the membrane can also be chosen depending on the used liquids, for example.

It is moreover preferred, if the membrane is made of materials which are chemical stable. The material must of course be chosen according to the liquids used. At the same time a biocompatibility between the membrane and the liquid further improves the quality of the liquid. Biocompatibility is generally understood as the quality of not having toxic or injurious effects on biological systems, like the human body.

In an example embodiment, the membrane is made out of a flexible material, for example a flexible plastic material. In a preferred embodiment, the membrane is made out of an elastic material.

Since the first part, the second part and the membrane due to their dimensions allow for an easy handling during a production process, the production of an apparatus according to claim 1 is further facilitated.

The first part and the membrane need not be permanently fixed to another. The first part only needs to be held, for example at a certain small distance, against the membrane, such that the sealing structure can still cause an interruption of the fluidic communication, for example by exerting a force through the membrane. The first part and the membrane may also be attached by any conventional means like gluing, thermo-bonding or laser welding, as there is no direct contact with the liquid on the side of the first part of the membrane. The second part and the membrane can also be attached to each other by thermo-bonding and/or laser welding. This way a tight sealing between the membrane and the second part can be provided without using additional agents found in glues, for example.

In general, permanent fixations between the first part and the membrane and the second part and the membrane are preferred.

According to a further embodiment said sealing structure is configured to press the membrane against the second part in order to interrupt said fluidic communication. By doing so, a simple way of interrupting the fluidic communication between the first opening and the second opening is provided. The sealing structure exerts a pressure on the membrane, which is consequently pushed toward or into the valve area. The pressure can be exerted by external electromechanical devices, so that the fluidic communication between the first and the second opening can be controlled electronically. The sealing structure may also contain mechanical structure, like any type of spring element, for example coil springs, cantilever springs, helical springs, flat springs and/or a stressed projection, which exerts the pressure. In this case the pressure of the liquid can be enlarged so that the pressure of the liquid can become larger than the pressure exerted by the mechanical structure. Then the membrane would be pushed back towards the first part and a fluidic communication between the first opening and the second opening would be established as long as the pressure in the liquid is high enough.

Preferably said sealing structure comprises a spring element and a retaining element, wherein said spring element is configured to press the retaining element against the membrane. This way the spring element exerts the pressure on the retaining element, which then exerts the pressure on the membrane. A spring element is understood to be any mechanical element, which can provide a constant force onto the retaining element. Preferably a flexible spring can be implemented into the first part, for example into a cut-out.

The retaining element can be adapted to the form of the valve area in order to press the membrane towards the valve area and efficiently interrupt the fluidic communication between the first and the second opening, meaning bringing the valve area in a sealed state.

Providing a spring element and a retaining element is further preferred, because the materials of the spring element and the retaining element can be independently chosen. The spring element needs to be rigid enough to exert a high enough pressure while the retaining element being in contact with the membrane must not damage the membrane. It is preferred, when the retaining element is connected to the first part only by the spring element, making it possible to precisely control the pressure exerted by the retaining element.

It is further preferred, when said sealing structure is an integral component of said first part. This way the production can be further facilitated. The first part can be produced by injection moulding, for example. By adjusting the materials accordingly the flexibility of the sealing structure, in particular of the spring element, can be maintained. It is also possible to implement further elements into the first part during the injection moulding, for example metal parts in the spring element.

According to another embodiment a valve seat is provided within said valve area by a first recess in the second part. The recess is easily producible during injection moulding of the second part or by carving out the recess of the second part. The recess allows for a room, into which the membrane can be pressed by the sealing structure and the valve seat allows for an abutting surface, against which the membrane can be pressed by the sealing structure. The second opening is preferably situated in the first recess and is located on the wall of said recess perpendicular to said abutting surface. This way the sealing structure cannot be pushed back towards the first part and cannot establishing a fluid communication between the first and the second opening, since any pressure exerted by the liquid from the second opening on the membrane and the sealing structure is substantially perpendicular to the possible displacement of the membrane and the sealing structure.

Accordingly the first opening is preferably provided in the abutting surface, so that the pressure applied by the liquid in the first opening can push the membrane and the sealing structure towards the first part establishing a fluid communication between the first and the second opening.

According to a further embodiment said valve area comprises a second recess within said first recess. The first recess is smaller than the first recess, so that a valve seat is still provided. The second recess can be produced like the first recess. The second recess is advantageous, since providing a first opening is facilitated. The first opening can be located anywhere within said second recess. Especially if the first opening needs to be connected with a fluidic structure or a reservoir containing a liquid, further connections are simplified. For example a cannula can be inserted into the second part, while one of its ends is situated within the second recess, providing the first opening. Thus further fluidic systems can be easily connected to the second end of said cannula being outside of the second part.

According to a further embodiment said second element further comprises a fluidic channel in form of a third recess. In order to further facilitate the production process the second part the second opening can be provided by a third recess. The recess preferably extends from the first recess and providing the second opening at the same time. If there is a fluidic connection between the first and the second opening, liquids can be pushed out of the valve area through this second opening and along the fluidic structure provided by the third recess. The sealing of the third recess of the second part is provided by the attached membrane which preferably also covers the third recess.

It is further preferred if said apparatus is configured to be implemented in a dispense interface. That means geometry and used materials need to be applicable in medical device like a dispense interface. It is further advantageous to provide means for fixing the apparatus within said dispense interface. Such means can be connectors such as snap locks, or the apparatus can be connected by form fit, force fit, or gluing.

It is further preferred if two of said apparatus are provided within one dispense interface. This way two medicaments from two separate reservoirs can be provided and separately controlled. The two fluidic channels originating from the two valve areas may combine within the dispense interface allowing the user to eject the two medicaments via a single dose dispenser.

The first part can be made of elastic material, in particular of polymers. This way the first part and the sealing structure can be produced as a single part. The sealing structure can thus be formed by an integrated structure. The integrated retaining element, for example, can be connected via an integrated spring to the first part. The material moreover allows for the flexibility of the sealing structure to press against the membrane and the second part.

If the retaining element comprises elastic material, in particular polymers, it is soft enough to be pressed against the membrane with a larger pressure to effectively seal the valve area, but at the same time without damaging the membrane. It is further preferred that the retaining element is made of elastic material, in particular of polymers.

The spring element can comprise the same or different polymers as said first part, and is in particular made of polymers. In using the same polymer as for the first part, the production is made more economic and faster. In using a different polymer than for the first part, the properties of the spring element can be adjusted independently. Different polymers can also be inserted into the spring element during injection molding of the first part with an integrated sealing structure.

To further adjust the properties of the spring element it is preferred, when the sealing structure, in particular the spring element, comprises metal or is made of metal. Especially steel inlays or elastomer parts are useful to adjust the properties of the spring element. They can also be inserted into the spring element during injection molding of the first part with an integrated sealing structure.

The contamination of the liquids can be further reduced, if the membrane is made of biocompatible polymers. This further provides an ideal sealing performance and a reversible geometry changes.

If the membrane is made of thermoplastic material, thermo-bonding of the membrane to the second part/and or to the first part can be performed. Especially thermo-bonding the membrane to the second part is advantageous, since a tight sealing can be achieved without the use of additional agents, which can be found in glues, for example.

The technical problem is also solved by a method for producing a valve element, comprising the steps of injection moulding a first part comprising a sealing structure, producing a second part and said second part comprising a valve area with a first opening and a second opening attaching a membrane to said second part via agent-free joining techniques and attaching said first part to said membrane, wherein said valve area is located in the area of said sealing structure, wherein said valve area is configured to allow for a fluidic communication between said first opening and said second opening and wherein said sealing structure is configured to allow for an interruption of said fluidic communication between said first opening and said second opening.

By providing said method, the sealing structure in this way is separated by the membrane from the fluidic structures. The materials, in particular of the sealing structure and the first part, can be arbitrarily chosen without risking contaminations of the liquids being guided by the fluidic structures by the chosen materials. Moreover to produce the valve element no small parts, which need to be implemented into the fluidic structure, need to be used.

Nevertheless small structures for a fluidic system of a valve element can be provided this way, so that the amount of dead volume storing unused fluid is kept minimal and at the same time using parts which are big enough to allow for an easy handling and assembly.

By inserting a cannula into said second part a first opening can be easily provided. One of its ends can be situated within the second recess, providing the first opening. Thus further fluidic systems can be easily connected to the second end of said cannula being outside of the second part.

As agent free joining techniques thermo bonding or laser welding is preferred. This way the fluidic structures can be kept clean from unwanted chemicals, while a tight attachement of the membrane to the second part can be guaranteed. For laser welding the material is preferably substantially transparent in the wavelength of the laser radiation.

If said first part and said sealing structure are produced as an integral part the method can be further facilitated. By injection molding for example the parts can be produced in one single step. Especially the retaining element and spring can be produced as an integral part with the first part.

If additional elements are inserted in said sealing structure during injection moulding of the first part, in particular in the spring element, a better adjustment of the properties of the sealing structure is possible. Especially elastomer parts and/or steel inlays are advantageous for this purpose.

Where applicable, for further embodiments and advantages of the Method the description of the apparatus applies accordingly.

BRIEF DESCRIPTION OF THE FIGURES

These as well as other advantages of various aspects of the present invention will become apparent to those of ordinary skill in the art by reading the following detailed description, with appropriate reference to the accompanying drawings, in which:

FIG. 12 illustrates different side views of the first part

FIG. 13 illustrates a perspective view of the first part, of the second part and of the membrane before assembly FIG. 14 illustrates a cross-sectional view of the first part, of the second part and of the membrane before assembly

DETAILED DESCRIPTION

Figure 1:
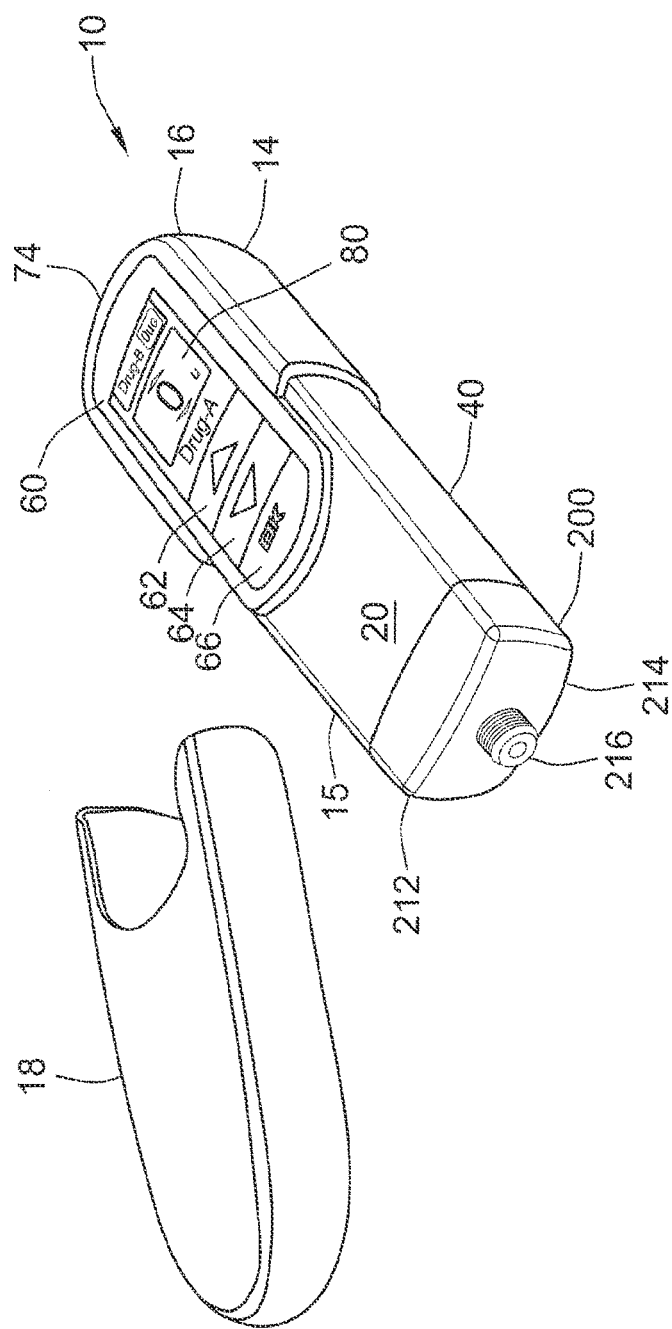
FIG. 1 illustrates a perspective view of the delivery device illustrated in FIG. 1a and 1b with an end cap of the device removed.
Figure 2:
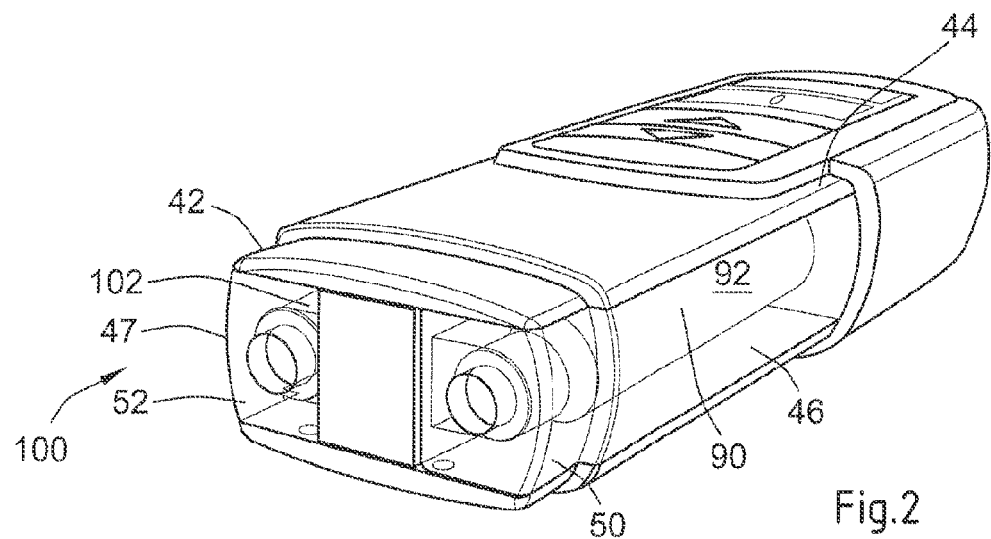
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
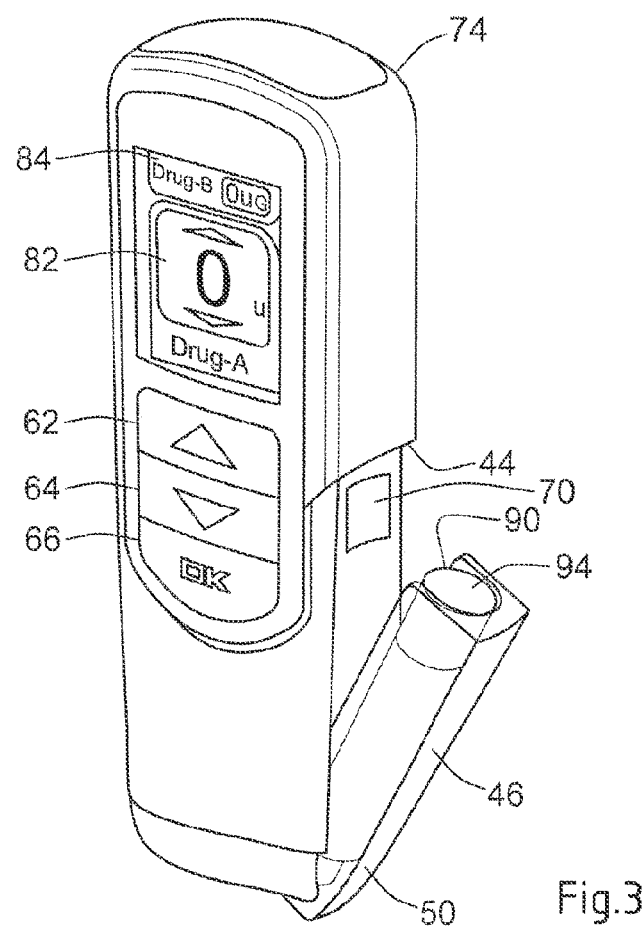
FIG. 3 illustrates a perspective view of the cartridge holder illustrated in FIG. 1 with one cartridge retainer in an open position.

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
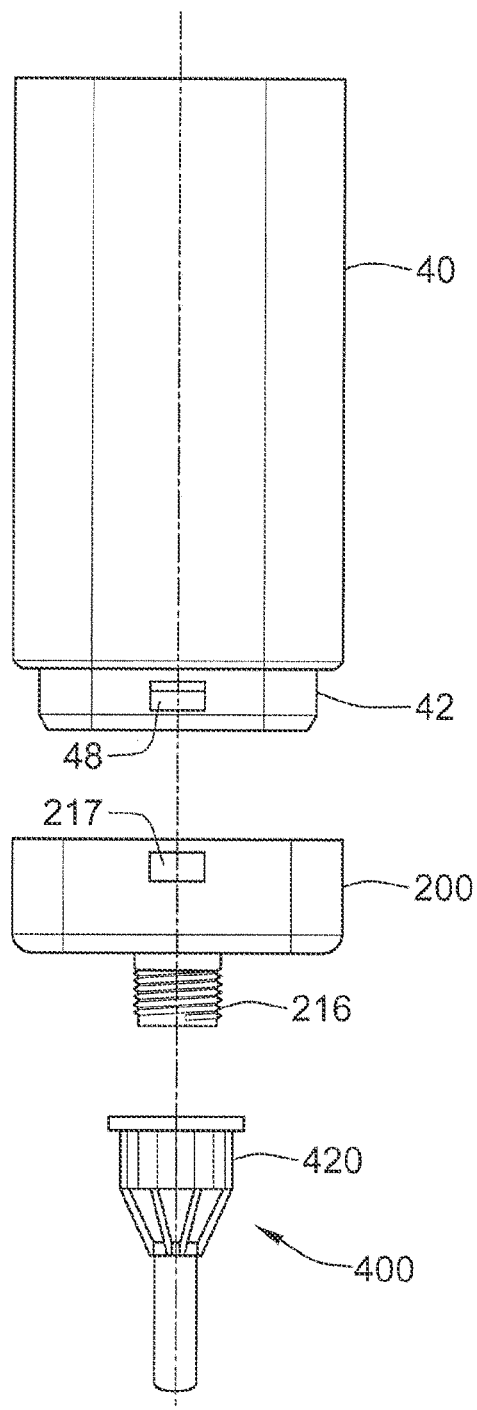
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
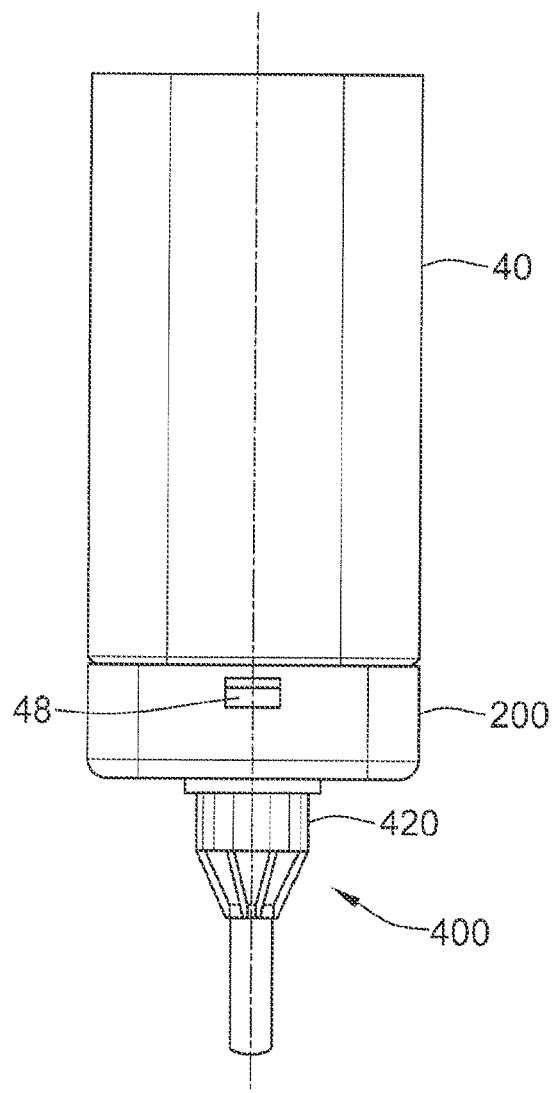
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
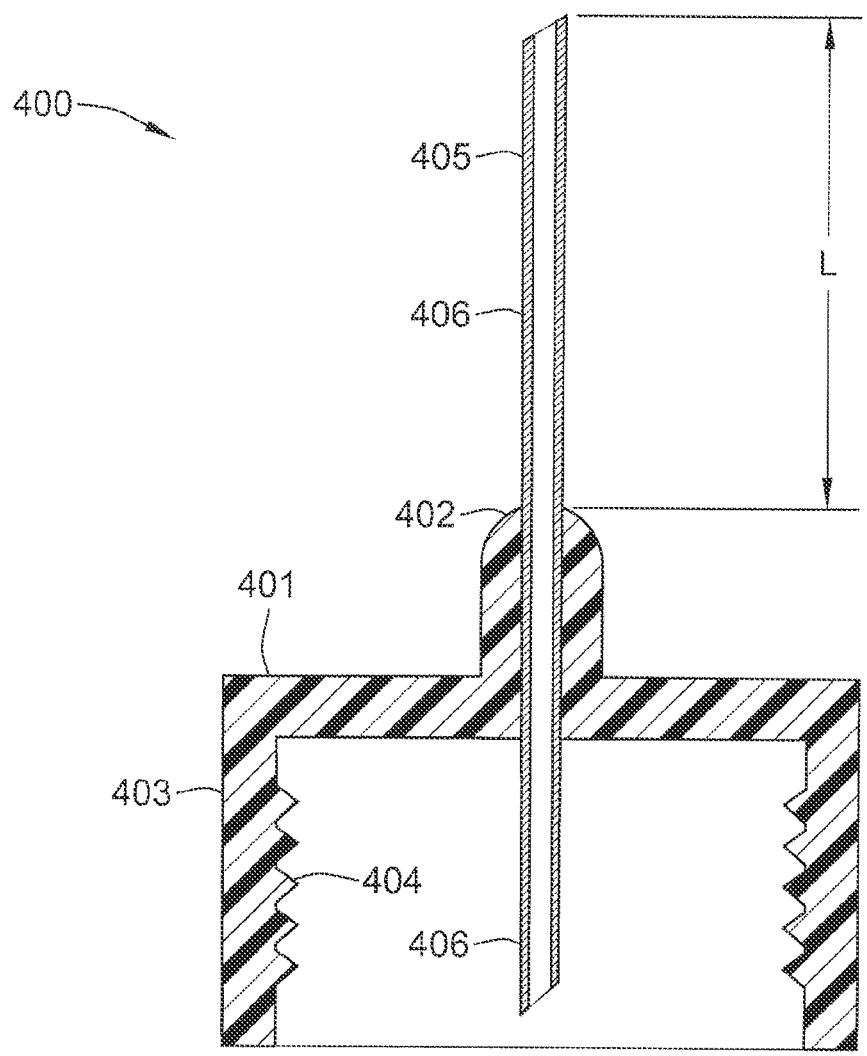
FIG. 6 illustrates one arrangement of the dose dispenser that may be mounted on a distal end of the delivery device.
Figure 7:
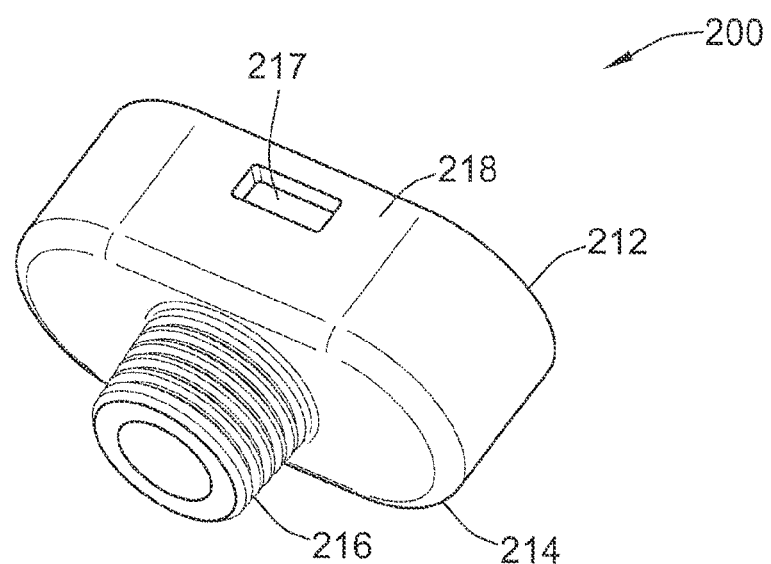
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

Figure 8:
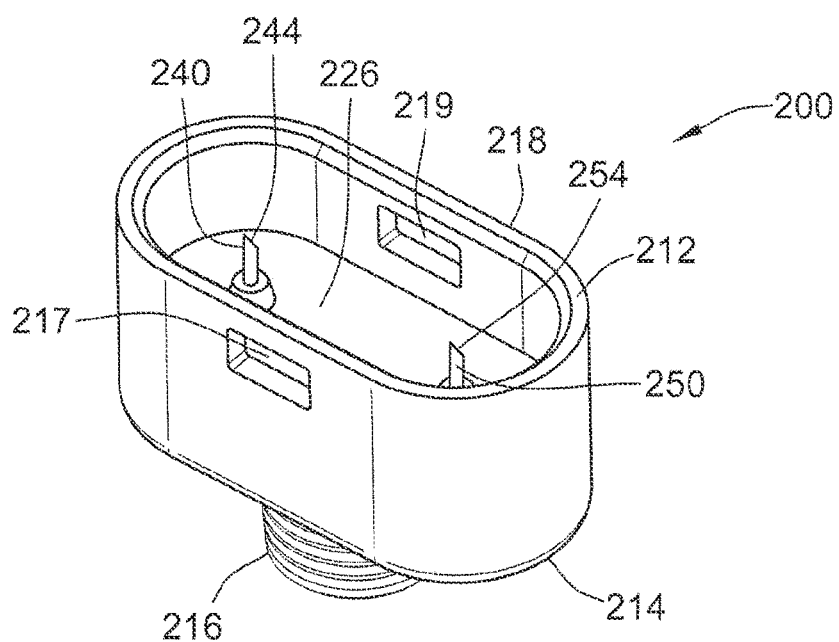
FIG. 8 illustrates another perspective view of the dispense interface illustrated in FIG. 4.
Figure 9:
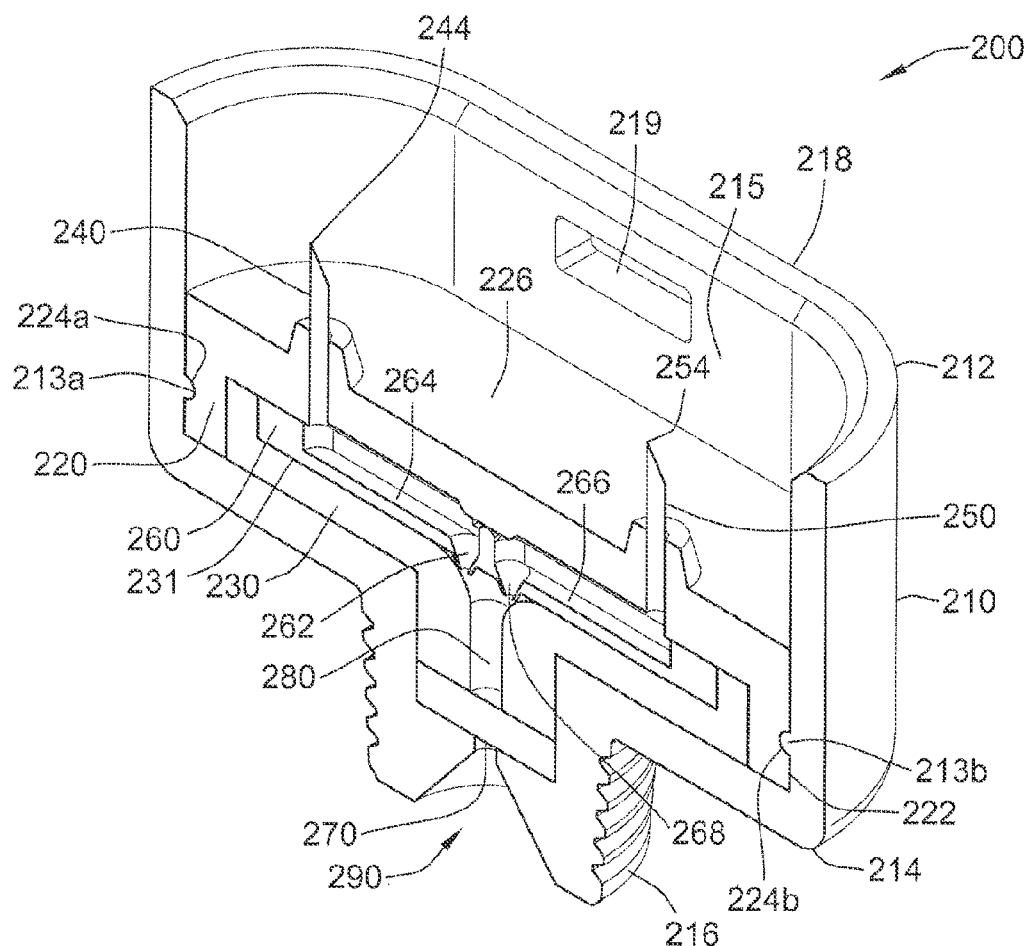
FIG. 9 illustrates a cross-sectional view of the dispense interface illustrated in FIG. 4.
Figure 10:
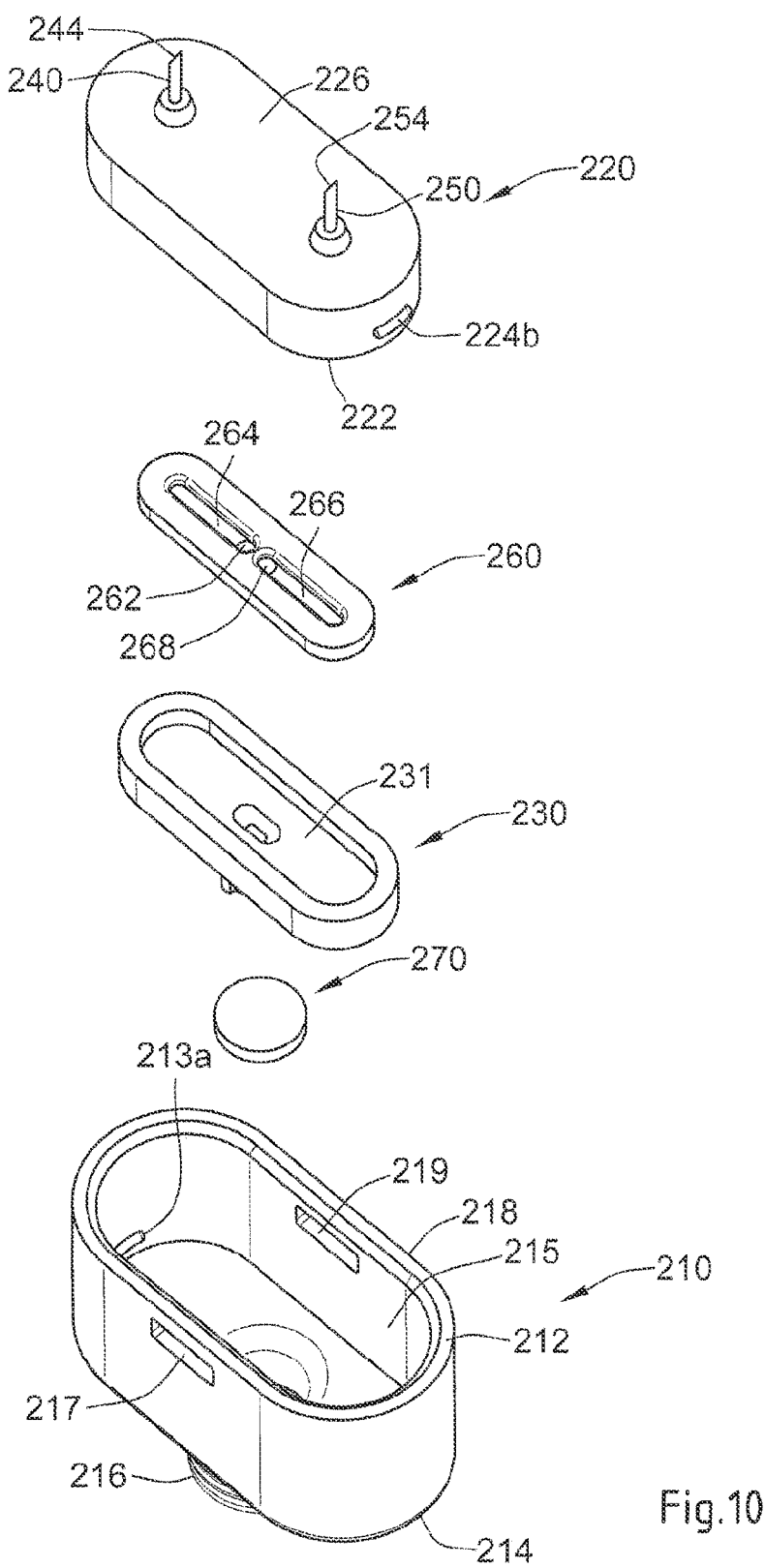
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
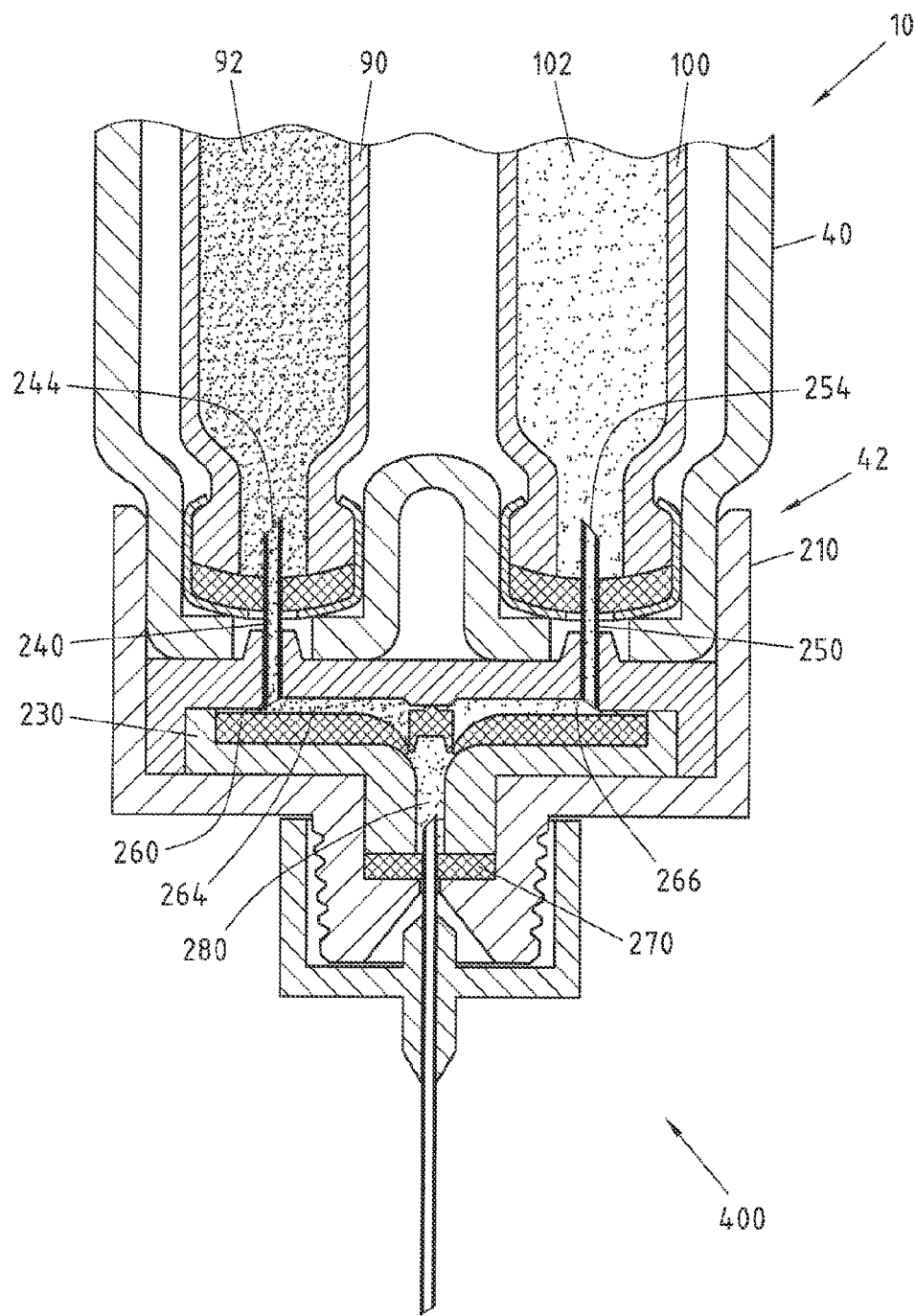
FIG. 11 illustrates a cross-sectional view of the dispense interface and dose dispenser mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

FIG. 12 illustrates different side views of the first part 300. FIG. 12a illustrates the first part 300 in a front view. The first part 300 comprises a spring element 302 and a retaining element 304 as sealing structure 302, 304. The retaining element 304 is connected to the first part 300 via the spring element 302. The retaining element 304 has a substantially cylindrical form, but any other form is possible as well. The first part 300 further comprises a cut-out 306, into which the spring element 302 is implemented. The spring element 302 in this state partially projects above the first part 300. Accordingly in this state the retaining element 304 is also projects the first part 300. It is possible though, that by application of high enough pressure on the retaining element 304, the retaining element 304 backs down and can be pushed at least partially into the cut-out 306 in the first part 300.

The first part 300, the spring element 302, and the retaining element 304 can each be made of the same elastic material, like polymer, or different materials, like different polymers. The spring element 302 may comprise additional elements like elastomer parts or steel inlays not shown, which can be preferably inserted into the spring element 302 during injection molding of the first part 300.

The spring element can be any type of typical spring element, like coil springs, cantilever springs, helical springs or flat springs, for example.

FIG. 12b illustrates the first part 300 illustrated in FIG. 12a from a side view. It can be clearly seen that the retaining element 304 protrudes from the first part 300.

FIG. 12c illustrates the first part 300 illustrated in FIG. 12a from a top view. The retaining element 304 protruding from the first part 300 and being connected over the spring element 302 is illustrated.

FIG. 13 illustrates a transparent perspective view of the first part 300, of the second part 310 and of the membrane 308 before assembly. The membrane 308 is made of a thin and flexible material, like polymers. This results in an optimal sealing performance and reversible geometry changes. The membrane has further a biocompatibility and acts as an impermeable barrier for liquids. A thermoplastic material fulfilling these requirements is preferred, since thermo-bonding can be used to attach the membrane 308 to the second part 310. Though, laser welding is also an option to perform said attachment.

The attachment of the membrane 308 and the first part 300 can be realised by the aforementioned means or by common means like gluing, since the liquid only comes into contact with the side of the membrane 308 facing the second part 310, but not with the side of the membrane 308 facing the first part 300.

Furthermore the second part comprises a valve area 312. This valve area 312 comprises a first recess 314 and a second recess 316 within said first recess 314. The first recess 314 provides a valve seat 318 and on its wall a second opening 320. The first recess 314 is designed in such a way, that the retaining element 304 can press the membrane 308 onto the valve seat 318. Thus the retaining element 304 has a smaller diameter than the first recess 314, but a bigger diameter than the second recess 316. The first recess 314 and the second recess 316 have a substantially cylindrical geometry. Any other geometry is possible as well, though. It is preferred, when the retaining element 304 and at least the first recess 314 have an adapted geometry. The second opening 320 in this case directly merges with a third recess 322 providing a fluidic channel. A cannula 324 is further inserted into the second part 310 providing a first opening 326. The cannula may be connected to a reservoir like the cartridges 90, 100 illustrated in FIG. 11. The cannulas may also be piercing needles 240, 250 as illustrated in FIG. 9 or 11.

A liquid or a medicament can enter the valve area 312 over the first opening 326, filling the second recess 316. If the pressure of the liquid entering the second recess 316 is too low, the force of the spring element 302 pushes the retaining element 304 with a part of the membrane 308 against the valve seat 318 creating a tight sealing of the second recess 316. The fluidic communication between the first opening 326 and the second opening 320 is interrupted.

If the force of the liquid against the membrane 308 becomes larger than the force, with which a part of the membrane 308 is pushed against the valve seat 318 by the retaining element 304 and the spring element 302, the part of the membrane 308 and the retaining element 304 are pushed toward the first part 300 and the liquid can enter the first recess 314. Since a second opening 320 is provided on the wall of the first recess 314, the fluid can enter the fluidic channel in form of the third recess 322.

If the pressure in the liquid falls under a certain level again, the force applied by the spring element 302 on the retaining element 304 and the according part of the membrane 308, the membrane 308 is pushed against the valve seat 318 again providing a tight seal.

The pressure changes of the liquid may be realised by pressurizing the cartridge 90, 100 containing the liquid.

In case the pressure in the fluidic system connected to the second opening 320 increases, a backflow of the fluid through the valve area 312 can be inhibited. If the retaining element 304 and the membrane 308 are pushed against the valve seat 318 the liquid in the fluidic channel in form of the third recess 322 can only apply a force on the membrane 308 an on the retaining element 304 substantially perpendicular to their possible displacement direction, since the spring element 302 and the geometry of the first recess 314 only allow for a displacement of the retaining element 304 in the direction of the cut out in the first part 300.

FIG. 14 illustrates a cross-sectional view of the first part 300, of the second part 310 and of the membrane 308 before assembly. It can be seen that if the first part 300 is attached to the membrane 308 and the membrane 308 is attached to the second part 310, the retaining element 304 presses the membrane 308 into the first recess 314 and onto the valve seat 318. It can be further seen, that the cannula 324 is inserted into the second part 310, so that one end of the cannula is inside the second recess 316 and provides the first opening 326.

The whole time the fluid does not come into contact with the first part 300 and in particular not with the sealing structure 302, 304, making it possible that the first part 300, the sealing structure 302, 304 and in particular the spring element 302 and/or the retaining element 304 may comprise materials, which are not biocompatible, for example.

Moreover it can be seen that a production devices comprising a valve element is facilitated in terms of economy and at the same time reducing or even eliminating the contamination of the liquid.

It is further possible to implement two valve elements comprising a first part 300, a second part 308 and a membrane 310 each in a dispense interface 200 to substantially replace non-return valves 262, 268.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus, comprising:
a first part comprising a sealing structure,
a membrane being held against said first part, and
a second part being attached to said membrane,
wherein said sealing structure comprises a spring element and a retaining element, wherein said spring element is configured to press the retaining element against the membrane,
wherein said spring element and said retaining element are produced as an integral part with the first part by injection moulding,
wherein said second part comprises a valve area with a first opening and a second opening, wherein said valve area comprises a valve seat and is located in the vicinity of said sealing structure, wherein said valve area is configured to allow for a fluidic communication between said first opening and said second opening, wherein said retaining element is configured to push said membrane against said valve seat to prevent said fluid communication, and wherein said retaining element and said membrane are configured to be moved away from said valve seat to allow said fluid communication.

2. The apparatus according to claim 1, wherein a said valve seat is provided within said valve area by a first recess in the second part.

3. The apparatus according to claim 2, wherein said valve area comprises a second recess within said first recess.

4. The apparatus according to claim 1, wherein said second element further comprises a fluidic channel in form of a third recess.

5. The apparatus according to claim 1, wherein said apparatus is configured to be implemented in a dispense interface.

6. The apparatus according to claim 1, wherein said sealing structure comprises metal.

7. The apparatus according to claim 1, wherein said membrane is made of biocompatible polymers.

8. A method for producing a valve element, comprising the steps of:

injection moulding a first part comprising a sealing structure, said sealing structure comprising a spring element and a retaining element produced as an integral part with the first part, producing a second part and said second part comprising a valve area with a first opening and a second opening, attaching a membrane to said second part via agent-free joining techniques, and attaching said first part to said membrane, wherein said valve area comprises a valve seat and is located in the vicinity of said sealing structure, wherein said valve area is configured to allow for a fluidic communication between said first opening and said second opening, wherein said retaining element is configured to push said membrane against said valve seat to prevent said fluid communication, and wherein said retaining element and said membrane are configured to be moved away from said valve seat to allow said fluid communication.

9. The method according to claim 8, wherein a cannula is inserted into said second part.

10. The method according to claim 8, wherein said agent free joining technique is thermo bonding or laser welding.

* * * * *